US008841400B2

(12) United States Patent
Henning et al.

(10) Patent No.: US 8,841,400 B2
(45) Date of Patent: Sep. 23, 2014

(54) USE OF ORGANOMODIFIED SILOXANES BRANCHED IN THE SILICONE PART FOR PRODUCING COSMETIC OR PHARMACEUTICAL COMPOSITIONS

(75) Inventors: Frauke Henning, Essen (DE); Juergen Meyer, Essen (DE); Christian Hartung, Essen (DE); Michael Ferenz, Essen (DE); Wilfried Knott, Essen (DE); Sascha Herrwerth, Essen (DE)

(73) Assignee: Evonik Degussa GmbH, Essen (DE)

( * ) Notice: Subject to any disclaimer, the term of this patent is extended or adjusted under 35 U.S.C. 154(b) by 95 days.

(21) Appl. No.: 13/262,872

(22) PCT Filed: Mar. 17, 2010

(86) PCT No.: PCT/EP2010/053422
§ 371 (c)(1),
(2), (4) Date: Oct. 4, 2011

(87) PCT Pub. No.: WO2010/118926
PCT Pub. Date: Oct. 21, 2010

(65) Prior Publication Data
US 2012/0027704 A1    Feb. 2, 2012

(30) Foreign Application Priority Data
Apr. 16, 2009 (DE) .................. 10 2009 002 417

(51) Int. Cl.
| | | |
|---|---|---|
| B01F 3/08 | (2006.01) |
| C08G 77/14 | (2006.01) |
| A61Q 5/02 | (2006.01) |
| A61Q 9/02 | (2006.01) |
| A61Q 19/10 | (2006.01) |
| A61Q 19/08 | (2006.01) |
| A61K 8/892 | (2006.01) |
| A61Q 19/00 | (2006.01) |
| A61Q 5/12 | (2006.01) |
| A61Q 17/04 | (2006.01) |
| C08G 77/04 | (2006.01) |
| A61K 8/894 | (2006.01) |
| A61Q 1/02 | (2006.01) |
| A61Q 19/04 | (2006.01) |
| B01F 17/54 | (2006.01) |
| C08G 77/00 | (2006.01) |

(52) U.S. Cl.
CPC ... *A61Q 19/00* (2013.01); *A61Q 5/02* (2013.01); *A61Q 9/02* (2013.01); *A61Q 19/10* (2013.01); *A61Q 19/08* (2013.01); *A61K 8/892* (2013.01); *A61Q 5/12* (2013.01); *A61Q 17/04* (2013.01); *C08G 77/80* (2013.01); *C08G 77/04* (2013.01); *A61K 8/894* (2013.01); *A61Q 1/02* (2013.01); *A61Q 19/04* (2013.01); *B01F 17/0071* (2013.01)

USPC .............. 528/31; 528/15; 528/29; 424/70.12; 516/23; 516/55

(58) Field of Classification Search
USPC ........... 528/15, 31, 29; 516/23, 55; 424/70.12
See application file for complete search history.

(56) References Cited

U.S. PATENT DOCUMENTS

| | | | |
|---|---|---|---|
| 5,474,712 A | 12/1995 | Dotolo et al. | |
| 5,817,302 A * | 10/1998 | Berthiaume et al. ....... | 424/70.12 |
| 5,879,671 A | 3/1999 | Halloran et al. | |
| 5,958,448 A * | 9/1999 | Ekeland et al. ............... | 424/450 |
| 7,196,153 B2 | 3/2007 | Burkhart et al. | |
| 7,442,666 B2 | 10/2008 | Herrwerth et al. | |
| 7,598,334 B2 | 10/2009 | Ferenz et al. | |
| 7,605,284 B2 | 10/2009 | Brueckner et al. | |
| 7,612,158 B2 | 11/2009 | Burkhart et al. | |
| 7,612,159 B2 | 11/2009 | Burkhart et al. | |
| 7,619,035 B2 | 11/2009 | Henning et al. | |
| 7,635,581 B2 | 12/2009 | Ferenz et al. | |
| 7,645,848 B2 | 1/2010 | Knott et al. | |
| 7,727,599 B2 | 6/2010 | Doehler et al. | |
| 7,754,778 B2 | 7/2010 | Knott et al. | |
| 7,825,205 B2 | 11/2010 | Knott et al. | |
| 7,825,206 B2 | 11/2010 | Neumann et al. | |
| 7,825,207 B2 | 11/2010 | Ferenz et al. | |
| 7,825,209 B2 | 11/2010 | Knott et al. | |
| 7,834,122 B2 | 11/2010 | Ferenz et al. | |
| 7,855,265 B2 | 12/2010 | Thum et al. | |
| 7,910,119 B2 | 3/2011 | Allef et al. | |

(Continued)

FOREIGN PATENT DOCUMENTS

| | | | |
|---|---|---|---|
| DE | 19603357 A1 | 8/1996 |
| DE | 10327871 A1 | 1/2005 |

(Continued)

OTHER PUBLICATIONS

Kollmeier, "Les Copolymeres Polysiloxanes polyethers commie additifs dans les formulations cosmetiques", Parfums, cosmetiques, aromes; 51; Jun.-Jul. 1983, pp. 67-72.

(Continued)

*Primary Examiner* — Margaret Moore
(74) *Attorney, Agent, or Firm* — Scully, Scott, Murphy & Presser, P.C.

(57) ABSTRACT

The invention relates to organomodified additives, emulsifiers, dispersants and/or active nourishing ingredients present in the silicon part of branched siloxane block copolymers, to the use thereof, in particular for producing cosmetic, dermatological or pharmaceutical formulations as well as care and cleansing products, and to the preparations as such. Specifically the invention relates to branched polysiloxanes having trifunctional T units as well as polyether groups, alkyl radicals of more than 7 carbon atoms or multi-hydroxy functional radicals.

15 Claims, No Drawings

(56) References Cited

U.S. PATENT DOCUMENTS

| | | | |
|---|---|---|---|
| 8,034,891 B2 * | 10/2011 | Okawa | 528/31 |
| 8,236,918 B2 * | 8/2012 | Mueh et al. | 528/38 |
| 2006/0155090 A1 | 7/2006 | Ferenz | |
| 2007/0123599 A1 | 5/2007 | Eilbracht et al. | |
| 2007/0128143 A1 | 6/2007 | Gruning et al. | |
| 2007/0178144 A1 | 8/2007 | Hameyer et al. | |
| 2007/0197678 A1 | 8/2007 | Cavaleiro et al. | |
| 2008/0004357 A1 | 1/2008 | Meyer et al. | |
| 2008/0108709 A1 | 5/2008 | Meyer et al. | |
| 2008/0125503 A1 | 5/2008 | Henning et al. | |
| 2008/0216708 A1 | 9/2008 | Herrwerth et al. | |
| 2008/0305065 A1 | 12/2008 | Ferenz et al. | |
| 2009/0137751 A1 | 5/2009 | Knott et al. | |
| 2009/0149573 A1 | 6/2009 | Venzmer et al. | |
| 2009/0189986 A1 | 7/2009 | Scheuermann et al. | |
| 2010/0022435 A1 | 1/2010 | Henning et al. | |
| 2010/0029587 A1 | 2/2010 | Bruckner et al. | |
| 2010/0031852 A1 | 2/2010 | Herrwerth et al. | |
| 2010/0034765 A1 | 2/2010 | Herrwerth et al. | |
| 2010/0041910 A1 | 2/2010 | Schubert et al. | |
| 2010/0055760 A1 | 3/2010 | Thum et al. | |
| 2010/0056649 A1 | 3/2010 | Henning et al. | |
| 2010/0056818 A1 | 3/2010 | Ferenz et al. | |
| 2010/0071849 A1 | 3/2010 | Knott et al. | |
| 2010/0081763 A1 | 4/2010 | Meyer et al. | |
| 2010/0081781 A1 | 4/2010 | Schubert et al. | |
| 2010/0105843 A1 | 4/2010 | Knott et al. | |
| 2010/0113633 A1 | 5/2010 | Henning et al. | |
| 2010/0168367 A1 | 7/2010 | Schubert et al. | |
| 2010/0184733 A1 | 7/2010 | Korevaar et al. | |
| 2010/0184913 A1 | 7/2010 | Ebbrecht et al. | |
| 2010/0248325 A1 | 9/2010 | Eckstein et al. | |
| 2010/0249339 A1 | 9/2010 | Henning et al. | |
| 2010/0266651 A1 | 10/2010 | Czech et al. | |
| 2010/0298455 A1 | 11/2010 | Henning et al. | |
| 2011/0021693 A1 | 1/2011 | Henning et al. | |
| 2011/0042004 A1 | 2/2011 | Schubert et al. | |
| 2011/0046305 A1 | 2/2011 | Schubert et al. | |

FOREIGN PATENT DOCUMENTS

| | | |
|---|---|---|
| DE | 102007055485 A1 | 6/2009 |
| DE | 102008001788 A1 | 11/2009 |
| DE | 102008041601 A1 | 3/2010 |
| EP | 0298402 B1 | 9/1992 |
| EP | 1125574 B1 | 6/2005 |
| EP | 1520870 B1 | 1/2006 |
| EP | 1 679 335 A2 | 7/2006 |
| EP | 1416016 B1 | 8/2008 |
| EP | 2 014 701 A2 | 1/2009 |
| EP | 2 159 248 A1 | 3/2010 |
| EP | 2 243 799 A1 | 10/2010 |
| WO | WO02053111 A2 | 7/2002 |
| WO | 2006/037380 * | 4/2006 |
| WO | 2007/135771 * | 11/2007 |
| WO | WO 2009/065644 A1 | 5/2009 |
| WO | WO 2009/138306 A1 | 11/2009 |

OTHER PUBLICATIONS

International Search Report dated Jun. 10, 2011 issued in PCT/EP2010/053422.

* cited by examiner

USE OF ORGANOMODIFIED SILOXANES BRANCHED IN THE SILICONE PART FOR PRODUCING COSMETIC OR PHARMACEUTICAL COMPOSITIONS

FIELD OF THE INVENTION

The invention relates to the use of organomodified siloxanes branched in the silicone part for producing cosmetic, dermatological or pharmaceutical compositions. In particular, the siloxanes are used as emulsifiers for W/O and O/W emulsions and also as hydrophilic and lipophilic care active ingredients for the care of human or animal body parts.

PRIOR ART

Organomodified siloxanes are used in a very wide variety of applications. Their properties can be adjusted inter alia through the type of modification, and also by the density of modification.

Thus, for example, it is possible to use allyl polyethers to attach organophilic or nonionic hydrophilic groups to a siloxane backbone. Compounds of this type are used, for example, as polyurethane foam stabilizers, as defoamers in fuels or as additives in paints and coatings.

In general, siloxanes can also be linked with lipophilic groups through reaction with e.g. α-olefins. The silicone waxes obtained in this way serve, for example, as additive in personal care applications.

It has been found in many fields of application that the effect of the siloxane is decisively dependent on the compatibility with the formulation in question.

Suitable cosmetic emulsifiers are, for example, siloxanes which also carry hydrophilic polyethers besides aliphatic, lipophilic groups based on α-olefins. A typical example to be mentioned here is the commercial product ABIL® EM 90 from Evonik Goldschmidt GmbH (Germany), which is characterized in particular by an excellent stabilization of water-in-oil (W/O) emulsions.

Siloxane-based emulsifiers for oil-in-water (O/W) have to have a more hydrophilic character, for which reason these products are generally pure polyether siloxanes.

EP 1125574 describes the use of relatively hydrophobic polyether siloxanes as O/W emulsifiers in which the polyether groups are located on the siloxane backbone in the α,ω position or terminal position. These structures are characterized by a long undisturbed silicone chain and therefore in particular by a velvety silky skin feel which they are able to incorporate into cosmetic emulsions.

A disadvantage of using these structures is the often inadequate emulsifiability. This inadequate emulsifiability can be attributed to the low degree of substitution since in linear structures of this type, only two modifications can be linked to a siloxane chain.

In order to increase the degree of modification per siloxane chain, but in so doing to retain the silicone character of the molecules, in the prior art (e.g. EP 0298402) branched structures have been produced with the help of crosslinking techniques. The number of possible branching units here is limited since in their synthesis it is not possible to use large amounts of the crosslinker without obtaining gelling-free products. Consequently, as a result of the synthesis, the targeted adjustment of high degrees of branching is not possible.

A further way of introducing branches into the siloxane structure is described in EP 1416016. Instead of the customary crosslinkers such as divinylsiloxanes or diolefins, mono-vinyl-functional siloxanes are used here for generating a branched silicone structure. However, this process has the disadvantage that mono-vinyl-functional siloxanes are costly to produce and are therefore not very accessible. Terminally functionalized siloxanes branched in the silicone part are not accessible by this process.

One object of the present invention was therefore to develop new types of organomodified siloxanes branched in the silicone part which can be used as high-performance additives for cosmetic and pharmaceutical formulations. This relates e.g. to emulsifiers, which can be used both in O/W and also in W/O emulsions, and are moreover able to combine a velvety silky skin feel with exceptional emulsifying properties.

U.S. Pat. No. 5,474,712 describes the use of polyethersiloxanes according to the prior art in conditioning shampoos for animals.

WO 02/053111 describes the use of silicone polyether block copolymers with $(AB)_n$ structures in aqueous, surface-active body cleaning compositions which have good cosmetic properties specifically for the volume, the combability and the shine of hair.

U.S. Pat. No. 5,879,671 describes the use of aqueous, surface-active body cleaning compositions which comprise mixtures of amino functional siloxanes and polyethersiloxanes according to the prior art as care active ingredient. These mixtures bring about a long-lasting improvement in the dry and wet combability of hair.

DE 19603357 describes the use of polyether-modified MQ resins (polyether dimethylsiloxysilicate) in cosmetic formulations as care active ingredients. These bring about a promotion in shine and retention of curls.

Siloxanes which carry pendent and/or terminal polyether groups are described as care active ingredient for hair and skin in the article "*Les Copolymeres Polysiloxanes polyethers comme additifs dans les formulations cosmetiques*" (Dr. Kollmeier; Parfums, cosmetiques, aromes; 51; 1983; 67-72).

Commercially available care active ingredients based on siloxane are, for example, ABIL® B 8842, ABIL® B 88183 and ABIL® B 8832 (Evonik Goldschmidt GmbH), Belsil® DMC 6031, Belsil® DMC 6032 and Belsil® DMC 6033 (Wacker-Chemie). The commercial product ABIL® B 8832 (Evonik Goldschmidt GmbH) is a siloxane terminally modified with polyether groups which is used as care active ingredient for hair and skin in surface-active solutions and care cosmetic formulations. The siloxanes terminally modified with polyether groups are a high-performance class of care active ingredients which bring about a marked conditioning effect for skin and hair from cosmetic formulations. In addition, these terminal siloxanes have foam-improving properties. However, as already described above, siloxanes with very long undisturbed siloxane backbone (for a good skin feel) and with more than two organic modifications (for compatibility in formulations) in these classic structures are not accessible.

A further object was therefore to develop compounds which, as hydrophilic or lipophilic care active ingredients, can improve the sensory properties of cosmetic and pharmaceutical formulations.

Moreover, these siloxanes should preferably have good compatibility with the formulation, be simple to incorporate (liquid at room temperature) and be able to be combined with conventional siloxanes in formulations.

Further objects not explicitly specified arise from the context of the description which follows, the examples and also the claims.

Surprisingly, it has been found that organomodified siloxanes branched in the siloxane part preparable by the process described in the previously unpublished patent applications DE 102008041601.0 and DE 102007055485.2 are suitable as additive in cosmetic, dermatological and pharmaceutical formulations. In particular, they are suitable as high-performance additives, emulsifiers and/or dispersion auxiliaries. Furthermore, they are suitable as care active ingredients for improving sensory properties of cosmetic, dermatological and pharmaceutical formulations.

The invention provides the use of organomodified siloxanes according to formula I branched in the siloxane part in cosmetic, dermatological and pharmaceutical formulations.

A further subject matter is formulations comprising organomodified siloxanes of the formula I branched in the silicone part themselves, and the use thereof.

$$M_a M'_b D_c D'_d T_e Q_f \quad \text{formula I}$$

wherein
$M=(R^1_3 SiO_{1/2})$
$M'=(R^2 R^1_2 SiO_{1/2})$
$D=(R^1_2 SiO_{2/2})$
$D'=(R^2 R^1 SiO_{2/2})$
$T=(R^3 SiO_{3/2})$
$Q=(SiO_{4/2})$
a=0 to 32; preferably 0 to 18, in particular 0 to 14;
b=0 to 32; preferably 0 to 18, in particular 1 to 14;
with the proviso that
a+b>2, preferably >3;
c=1 to 600, preferably 10 to 500, in particular 20 to 400;
d=0 to 80, preferably 0 to 60, in particular 3 to 40;
e=0 to 30, preferably 1 to 20, in particular 2 to 15;
f=0 to 15, preferably 1 to 12, in particular 2 to 10;
with the proviso that
e+f≥1, preferably ≥2, in particular ≥3;
$R^1$=independently of one another, identical or different linear or branched, optionally aromatic hydrocarbon radicals having 1 to 16 carbon atoms, preferably methyl or phenyl, in particular methyl;
$R^2$=independently of one another, identical or different linear or branched alkyl radicals having more than 7 carbon atoms, SiC- or SiOC-bonded polyether radicals or SiC- or SiOC-bonded multi-hydroxy functional radicals, preferably polyether radicals of the general formula IIa, IIb or IIc or multi-hydroxy-functional radicals of the formula IIIa or IIIb:

$$-CH_2-CH_2-(CH_2)_n O(EO)_x (PO)_y (XO)_z R^4 \quad \text{[formula IIa]},$$

$$CH_2=CH-(CH_2)_n O(EO)_x (PO)_y (XO)_z- \quad \text{[formula IIb]},$$

$$R^4-O- \quad \text{[formula IIc]}$$

where
$EO=(C_2 H_4 O)$;
$PO=(C_3 H_6 O)$;
$XO=(C_2 H_3 R^5 O)$;
n=0 to 9, in particular 1;
x=0 to 50, in particular 5 to 30;
y=0 to 50, in particular 2 to 20;
z=0 to 10, in particular 0;
$R^4$=independently of one another, identical or different radicals selected from the group comprising: H, alkyl radicals having 1 to 16 carbon atoms, or acyl radicals;
$R^5$=independently of one another, identical or different radicals selected from the group comprising: alkyl radicals having 2 to 16 carbon atoms, which may optionally be interrupted by ether functions, alkaryl radicals having 7 to 18 carbon atoms, aryl radicals having 6 to 16 carbon atoms, preferably ethyl or phenyl;

$$R^6 A_g B^1_h B^2_i C_j \quad \text{[formula IIIa]},$$

$$A_g B^1_h B^2_i R^7 \quad \text{[formula IIIb]},$$

where
$R^6$=linear or branched alkylene radical, preferably $-CH_2-CH_2-(CH_2)_n-$, in particular $-CH_2-CH_2-CH_2-$;
$R^7$=linear or branched, unsaturated alkenylene radical, preferably $CH_2=CH-(CH_2)_n-$, in particular $CH_2=CH-CH_2-$;

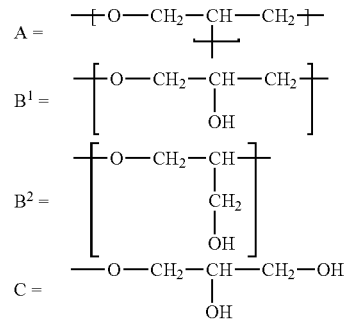

g=0 to 20, preferably 0 to 5, in particular 0 to 3;
h=0 to 20, preferably 0 to 5, in particular 0 to 3;
i=0 to 20, preferably 0 to 5, in particular 0 to 3;
j=1 to 21, preferably 1 to 6, in particular 1 to 4;
$R^3$=independently of one another, identical or different radicals $R^1$ or $R^2$, preferably $R^1$, in particular methyl, dodecyl or hexadecyl.

Within the context of this invention, multi-hydroxy-functional means that the radical of the formula IIIa itself carries at least two hydroxy groups; if the group C occurs more than once, that at least two hydroxyl groups are introduced per group C into the structure and thus a large number of hydroxyl groups are present on average in the product mixtures.

A further subject matter of the invention is the use of organomodified siloxanes branched in the silicone part in cosmetic, dermatological and pharmaceutical formulations, characterized in that these siloxanes are prepared by hydrosilylation of α-olefins, unsaturated polyether or glycerol derivatives with SiH-functional siloxane block copolymers branched in the silicone part and liquid at a temperature of 25° C. and a pressure of 101 325 Pa, where the siloxane block copolymers have been prepared by reacting a mixture comprising
a) one or more SiH-functional siloxanes,
b) one or more SiH-function-free siloxanes and
c) one or more tetraalkoxysilanes, and optionally
d) one or more trialkoxysilanes
with the addition of water and in the presence of at least one solid Brönsted-acidic catalyst, which is selected from the acidic ion exchangers, in one process step.

This preparation process of the SiH-functional siloxane block copolymers is described in the patent applications DE 102008041601.0 and DE 102007055485.2.

The previously unpublished German patent applications DE 102008041601.0 and DE 102007055485.2 are considered in their entirety to form part of the disclosure of this application.

Controlled via the reaction conditions, such as for example the amount of water or the reaction temperature, the siloxanes branched in the silicone part can also have residual fractions of alkoxy groups.

Despite the high degree of branching and at times high molecular weights, the structures according to the invention have a comparatively low viscosity, meaning that they are readily processable. The viscosities of these compounds are below 25 000 mPas.

Siloxane preparations or compositions according to the invention are suitable inter alia as emulsifiers which have excellent emulsifying and emulsion-stabilizing properties. In order to be suitable as an emulsifier, a certain balance between hydrophobicity and hydrophilicity has to be established through the organomodification. A further subject matter is therefore the use of the siloxanes described above as emulsifiers, in particular in oil-in-water (O/W) and/or water-in-oil (W/O) emulsions.

It has been found that these siloxanes are particularly suitable for pigment-containing formulations as emulsifier if the hydrophilic modification thereof is a multi-hydroxy-functional radical of the formula IIIa or IIIb. One subject matter is therefore also the use of the compounds according to the invention with multi-hydroxy-functional modification according to formula IIIa for the stabilization of pigment-containing formulations. In particular, inorganic or organic pigments and/or inorganic or organic particles may be present.

Moreover, the siloxanes are suitable in the preparations or compositions according to the invention as additives for cosmetic and pharmaceutical formulations for improving their sensory properties. The systems used as emulsifier also make it possible to incorporate a velvety silky skin feel into cosmetic formulations. This is important since consumers are increasingly placing importance on the fact that cosmetic formulations can not only be spread easily and readily absorb into the skin, but that, following absorption, a smooth, soft, velvety impression is left. The use of the siloxanes according to the invention as additives for cosmetic and pharmaceutical formulations for improving their sensory properties is therefore a further subject matter of this invention.

Advantages of the use according to the invention are that the siloxanes can be used as high-performance emulsifiers and as high-performance care active ingredients. In this connection, they bring about a marked conditioning effect for skin and hair. As a result of this conditioning effect on, for example, the skin, a dry, harsh or rough condition of the skin can be prevented following applications of the formulation, and a pleasant, velvety-silky skin feel is achieved.

It is a further advantage that the use according to the invention as care active ingredient contributes to improved foaming behavior, an increased foam volume and better foam creaminess of the formulations.

It is a further advantage that the siloxanes used are easy to process since they are liquid or can readily be liquefied at room temperature and can be combined with conventional constituents of cosmetic and pharmaceutical formulations.

As regards the quality and storage stability of the end products, the preparation process described in DE 102008041601.0 and DE 102007055485.2 has the advantage that the branched hydrogen siloxanes produced according to the invention and the secondary products produced therefrom have no or little tendency towards gelling and can thus be stored over a prolonged period without the viscosity of the products changing to a substantial degree. This advantage is to be emphasized specifically in the case of high molecular weight products. The products according to the invention are thus based primarily on organomodified siloxanes branched in the silicone part and thus highly branched and also relatively high molecular weight (average molar mass>3000 g/mol), but at the same time gel-free and thus comparatively low viscosity (dynamic viscosity<25 000 mPas) structures.

A further advantage of the siloxanes according to the invention is that the advantages of laterally modified siloxanes and of α,ω-modified siloxanes are present together, and a relatively high degree of modification in the sense of a larger number of substitution options is present compared to purely linear structures. As a result, structures with a long undisturbed siloxane backbone are accessible which are able to introduce a particularly good skin feel into cosmetic, dermatological and pharmaceutical formulations. The formulations are characterized by a velvety-silky and not very oily skin feel.

The unsaturated organic compounds, which have at least one double bond per molecule, used for the organomodification of the siloxanes that can be used are e.g. α-olefins, vinylpolyoxyalkylenes, allylpolyoxyalkylenes, glycerol monoallyl ethers and/or polyglycerol monoallyl ethers. Preference is given to using vinylpolyoxyalkylenes and/or allylpolyoxyalkylenes. Particularly preferred vinylpolyoxyalkylenes are e.g. vinylpolyoxyalkylenes with a molecular weight in the range from 100 g/mol to 5000 g/mol, which can be composed of the monomers propylene oxide, ethylene oxide, butylene oxide and/or styrene oxide in blockwise or random distribution and which may be end-capped either hydroxy-functionally or by a methyl ether function or an acetoxy function. Particularly preferred allylpolyoxyalkylenes are e.g. allylpolyoxyalkylenes with a molecular weight in the range from 100 g/mol to 5000 g/mol, which may be composed of the monomers propylene oxide, ethylene oxide, butylene oxide and/or styrene oxide in blockwise or random distribution and which may be end-capped either hydroxy-functionally or else by a methyl ether function or an acetoxy function. Furthermore, glycerol monoallyl ethers and polyglycerol monoallyl ethers can be used particularly preferably.

The precious-metal-catalyzed hydrosilylation of the branched hydrogen siloxanes with these unsaturated organic compounds can be carried out e.g. as described in the prior art, e.g. in EP 1520870. The specification EP 1520870 is hereby incorporated by reference and forms part of the disclosure of the present invention. The platinum-catalyzed hydrosilylation has a high selectivity during the formation of the desired SiC bonds. However, depending on the reaction conditions, secondary reactions such as, for example, a dehydrogenative SiOC linkage of the SiH groups with hydroxy groups or else a hydrolysis and condensation reaction can lead to the formation of by-products, which are described in more detail by the formulae IIb, IIc and IIIb.

It is apparent that by mixing the organo- and in particular polyether-modified, branched siloxanes with unbranched siloxanes, it is possible to obtain mixtures which are valuable surface-active ingredients but which, depending on the mixing ratio, can have in total less than one branching unit per molecule.

Use:

The use of the preparations according to the invention is described below by way of example, without any intention to limit the invention to these exemplary embodiments. Where ranges, general formulae or compound classes are given below, then these are intended to include not only the corresponding ranges or groups of compounds explicitly mentioned, but also all part ranges and subgroups of compounds which can be obtained by removing individual values (ranges) or compounds. Where documents are cited within the context of the present description, then their contents should in their entirety form part of the disclosure of the present invention.

Unless explicitly stated otherwise, all percentage data in the description below or the examples is to be understood as being based on the weight.

Use as Emulsifiers:

The emulsifier formulations according to the invention are preferably used as oil-in-water, water-in-oil or water-in-silicone emulsifiers or dispersion auxiliaries. The present invention therefore also provides dispersions or emulsions comprising inorganic or organic pigments or particles and comprising at least one of the emulsifiers according to the invention.

The emulsifier is preferably also used for producing O/W impregnation emulsions for textiles. The textiles are preferably wet wipes, particularly preferably cosmetic wet wipes.

The emulsions and dispersions according to the invention comprise, based on the total mass, more mass percent of oil component than the sum of the mass percentages of emulsifier, surfactant and optionally coemulsifier.

Consequently, the oil-in-water, water-in-oil and water-in-silicone emulsions and dispersions obtained with the help of the emulsifier formulations according to the invention, and also O/W impregnation emulsions for textiles are likewise subject matter of the invention. The textiles impregnated with O/W impregnation emulsions according to the invention are likewise subject matter of the invention. These are characterized by a good cleaning performance and a pleasant velvety-smooth skin feel.

A further subject matter of the invention is the use of the emulsifier formulations according to the invention for producing cosmetic, dermatological or pharmaceutical formulations. The use of the emulsions and dispersions according to the invention for producing cosmetic, dermatological or pharmaceutical formulations is likewise subject matter of the invention.

Consequently, the cosmetic, dermatological or pharmaceutical formulation comprising at least one emulsifier formulation according to the invention or at least one emulsion or dispersion according to the invention is likewise subject matter of the invention.

A further subject matter of the invention is the use of the emulsifier formulations or of the emulsion or dispersion according to the invention for producing care and cleaning compositions, optionally comprising dispersed solids, for the home or industry, in particular for hard surfaces, leather or textiles. Consequently, the care and cleaning compositions for the home or industry and the care and cleaning compositions for hard surfaces, leather or textiles are likewise subject matter of the invention.

The cosmetic, dermatological or pharmaceutical formulations according to the invention and also the care and cleaning compositions can comprise e.g. at least one additional component selected from the group of the emollients, emulsifiers and surfactants, thickeners/viscosity regulators/stabilizers, UV photoprotective filters, antioxidants, hydrotropes (or polyols), solids and fillers, film formers, pearlescent additives, deodorant and antiperspirant active ingredients, insect repellents, self-tanning agents, preservatives, conditioners, perfumes, dyes, cosmetic active ingredients, care additives, superfatting agents, solvents.

Substances which can be used as exemplary representatives of the individual groups are known to the person skilled in the art and can be found for example in the German application DE 102008001788.4. This patent application is hereby incorporated by reference and thus forms part of the disclosure.

In one preferred embodiment, the cosmetic, dermatological or pharmaceutical formulations according to the invention and also the care and cleaning compositions comprise, as additional component, pigments (e.g. $TiO_2$, $FeO_x$, ZnO, mica and for example those which are listed under UV filter substances and solids) or particles (e.g. silicone elastomers, nylon-12, PMMA, boron nitride and for example those which are listed under UV filter substances and solids).

In a likewise preferred embodiment, the cosmetic, dermatological or pharmaceutical formulations according to the invention and also the care and cleaning compositions comprise cosmetic active ingredients as additional component.

Preference is given to the use of emulsifier formulations according to the invention or of the emulsion or dispersion according to the invention for producing cosmetic or pharmaceutical formulations.

The emulsifier formulations and preparations according to the invention can be used, depending on their hydrophilicity, either in the form of W/O, or else in the form of O/W emulsifier formulations.

Possible application forms of the emulsions and dispersions comprising the emulsifier formulations according to the invention are therefore sprays, lotions, creams, ointments and thus use over a very broad consistency range from water-thin to extremely pasty, in the extreme case even solid, is possible.

Consequently, the emulsifier formulations and preparations can be used for example in care creams and lotions for face, body and hands, in sunscreen emulsions, in make-up, in aerosols, roll-ons, pump sprays, sticks e.g. in the antiperspirant/deodorant sector, in babycare products, in intimate care, footcare, haircare, nail care, dental care or oral care products, and also in dermatological ointments.

Use as Lipophilic Care Active Ingredients:

The silicone products according to the invention are moreover preferably used as lipophilic emollients. Subject matter of the present invention is therefore also cosmetic formulations in which the silicone products according to the invention are used as additive for improving the sensory properties. The hydrophobic emollients/care active ingredients are preferably dissolved in the oil phase of the cosmetic formulation. Silicone products which have been modified with lipophilic substituents such as e.g. alkyl groups are primarily used here.

Use as Hydrophilic Care Active Ingredients:

A further constituent of the invention is care formulations comprising the care active ingredients according to the invention.

The silicone products according to the invention are used inter alia also preferably as hydrophilic emollients. The present invention therefore also provides cosmetic formulations in which the silicone products according to the invention are used as additive for improving the sensory properties. For this application, an adequate solubility in water or emulsifiability in water of the silicone products is necessary, meaning that products modified in particular with polyether groups are used here.

Preferably, the care formulations comprise from 0.01 mass percent to 20 mass percent, preferably 0.05 mass percent to 10 mass percent, particularly preferably 0.1 mass percent to 3 mass percent, of care active ingredient, based on the total mass of the care formulation.

Preference is likewise given to aqueous, particularly preferably aqueous, surface-active care formulations.

Preferably, these care formulations are cosmetic, dermatological or pharmaceutical formulations.

These may be for example: shower baths and shower gels, bath formulations, liquid soaps and shampoos, skin masks, shaving foams, hair rinses, leave-in conditioners and styling products for hair, where the term hair is also to be understood as meaning fur and hide.

The care formulations according to the invention can, as described above, comprise e.g. at least one additional component as in application DE 102008001788.4.

Care formulations according to the invention can be used as skincare product, face care product, head care product, bodycare product, intimate care product, footcare product, haircare product, nail care product, dental care product or oral care product.

Care formulations according to the invention can be used in the form of an emulsion, a suspension, a solution, a cream, an ointment, a paste, a gel, an aerosol, a spray, a cleaning product, a make-up or sunscreen preparation of a facial toner.

Care formulations corresponding to the present invention have a conditioning effect on skin and hair, where the term hair is also to be understood as including fur or hide.

The invention therefore provides the use of compounds according to the invention and their formulations for the conditioning of skin and/or hair; a further subject matter of the invention is the use of formulation according to the invention for imparting a pleasant, velvety silky skin feel and for avoiding a dry or harsh condition of the skin; a yet further subject matter of the invention is the use of formulation according to the invention for improving at least one property of the hair selected from the group: combability, softness, ability to be shaped, manageability, detanglability, volume, shine.

Care formulations according to the invention reduce the roughness of stressed skin. The invention therefore further provides the use of the formulations according to the invention for reducing skin roughness.

The invention further provides preparations comprising organomodified siloxanes of the formula I branched in the silicone part.

A further subject matter of the invention is preparations comprising organomodified siloxanes of the formula I branched in the silicone part, where b is greater than or equal to 1 and d is 0, and also preparations in which the organomodification is a polyether radical of the general formula IIa or a glycerol derivative of the general formula IIIa.

The invention further provides cosmetic, dermatological or pharmaceutical formulations comprising at least one of the preparations or formulations in the form of an emulsion.

The invention further provides care and/or cleaning compositions for the home, for hard surfaces, leather or textiles, comprising at least one of the aforementioned preparations or formulations in the form of an emulsion.

The invention further provides cosmetic, dermatological or pharmaceutical formulations or preparations in the form of care and cleaning compositions comprising particles or pigments as additional component.

The invention further provides cosmetic, dermatological or pharmaceutical formulations or preparations in the form of care and/or cleaning compositions comprising cosmetic active ingredients as additional component.

Further subject matters of the invention arise from the claims, the disclosure of which, in its entirety, is part of the description.

EXAMPLES

In the examples listed below, the present invention is described by way of example without any intention to limit the invention, the scope of application of which arises from the entire description and the claims, to the embodiments specified in the examples. Where ranges, general formulae or compound classes are stated below, then these are intended to include not only the corresponding ranges or groups of compounds explicitly mentioned, but also all part ranges and subgroups of compounds which can be obtained by removing individual values (ranges) or compounds. Where documents are cited within the context of the present description, then their contents are intended, in their entirety, to form part of the disclosure of the present invention. If, within the context of the present invention, compounds such as e.g. organomodified polysiloxanes or polyoxyalkylene, are described which may have different monomer units several times, then these can occur in these compounds in random distribution (random oligomer) or arranged (block oligomer). Data relating to the number of units in such compounds is to be understood as a statistical average value, averaged over all of the corresponding compounds. Within the context of this invention, emulsifier formulation is to be understood as meaning an emulsifier which comprises at least one substance of the general formula (I) and optionally at least one co-emulsifier.

General Working Instructions I (GWI I) for Producing Polyether-, Alkyl- and/or Glycerol-Modified Siloxanes According to Formula I:

$$M_a M'_b D_c D'_d T_e Q_f \qquad \text{formula I}$$

where $M=(R^1_3SiO_{1/2})$ $M'=(R^2R^1_2SiO_{1/2})$ $D=(R^1_2SiO_{2/2})$ $D'=(R^2R^1SiO_{2/2})$ $T=(R^3SiO_{3/2})$ $Q=(SiO_{4/2})$ where $R^1$=methyl, $R^2$, $R^3$: see Table 1.

In a four-neck flask provided with precision-ground glass stirrer, dropping funnel, internal thermometer and reflux condenser, 1.3·(b+d) mol of α-olefin and/or allyl polyether and/or glycerol monoallyl ether and 10 ppm of Karstedt catalyst were introduced as initial charge and heated to 90° C. under a nitrogen atmosphere. 1 mol of the SiH-siloxane of the general formula IV $$[Me_3SiO_{1/2}]_a[Me_2HSiO_{1/2}]_b[Me_2SiO_{2/2}]_c[MeH SiO_{2/2}]_d[R^3SiO_{3/2}]_e[SiO_{4/2}]_f \qquad \text{formula IV}$$

(prepared in accordance with instructions in patent applications DE 102008041601.0 and DE 102007055485.2) was added dropwise and the mixture was stirred for 2 h at 90° C. According to the SiH value determination, complete conversion of the SiH-siloxane was obtained. In each case, a viscous, clear to slightly cloudy, virtually colorless product was obtained.

Table 1 lists the siloxanes prepared according to these general instructions GWI I.

TABLE 1

Prepared polyether-, alkyl- and/or glycerol-modified silicone products according to formula I ($R^1$ = methyl)

| Product No. | Modification $R^2$ —CH₂CH₂CH₂O(EO)ₓ(PO)ᵧR⁴ | | | $R^3$ | a | b | c | d | e | f |
|---|---|---|---|---|---|---|---|---|---|---|
| | x | y | $R^4$ | | | | | | | |
| 1 | 10 | 10 | H | $CH_3$ | 0 | 7 | 78 | 0 | 5 | 0 |
| 2 | 10 | 10 | H | $CH_3$ | 0 | 7 | 138 | 0 | 5 | 0 |
| 3 | 10 | 10 | H | $CH_3$ | 0 | 7 | 238 | 0 | 5 | 0 |
| 4 | 10 | 10 | H | $CH_3$ | 0 | 5 | 142 | 0 | 3 | 0 |
| 5 | 21 | 5 | H | $CH_3$ | 0 | 7 | 138 | 0 | 5 | 0 |
| 6 | 13 | 0 | H | $C_{16}H_{33}$ | 0 | 7 | 138 | 0 | 5 | 0 |
| 7 | 0 | 17 | $CH_3$ | $CH_3$ | 0 | 7 | 238 | 0 | 5 | 0 |
| 8 | 10 | 10 | H | $CH_3$ | 6 | 4 | 133 | 4 | 0 | 3 |
| 9 | —CH₂CH₂CH₂OCH₂CH(OH)CH₂OH | | | $C_{16}H_{33}$ | 0 | 7 | 138 | 0 | 5 | 0 |
| 10 | —CH₂CH₂CH₂OCH₂CH(OH)CH₂OH | | | $CH_3$ | 0 | 7 | 238 | 0 | 5 | 0 |
| 11 | $C_{16}H_{33}$ | | | $CH_3$ | 0 | 7 | 238 | 0 | 5 | 0 |
| Comparative example: | | | | | | | | | | |
| 12 | 21 | 5 | H | $CH_3$ | 2 | 0 | 75 | 5 | 0 | 0 |

General Working Instructions II (GWI II) for Producing Mixed Alkyl- and Polyether-Modified or Mixed Alkyl- and Glycerol-Modified Siloxanes According to Formula I:

$$M_a M'_b D_c D'_d T_e Q_f \quad \text{formula I}$$

where
$M = (R^1_3 SiO_{1/2})$
$M' = (R^2 R^1_2 SiO_{1/2})$
$D = (R^1_2 SiO_{2/2})$
$D' = (R^2 R^1 SiO_{2/2})$
$T = (R^3 SiO_{3/2})$
$Q = (SiO_{4/2})$ where
$R^1 = R^3$ = methyl,
$R^2$: see Table 2.

In a four-neck flask provided with precision-ground glass stirrer, dropping funnel, internal thermometer and reflux condenser, 1.3·(b+d)·o mol of α-olefin and 1.3·(b+d)·p mol of allyl polyether and/or glycerol monoallyl ether (where o+p=1) and 10 ppm of Karstedt catalyst (based on the raw materials without solvents) in ca. 30% toluene (based on the total initial weight) were introduced as initial charge and heated to 90° C. under a nitrogen atmosphere. 1 mol of the branched SiH-siloxane of the general formula V

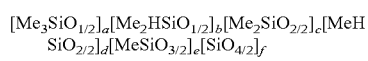

formula V (prepared in accordance with instructions in patent applications DE 102008041601.0 and DE 102007055485.2) was added dropwise and the mixture was stirred for 2 h at 90° C. According to SiH value determination, complete conversion of the SiH-siloxane was obtained. Volatile fractions were then distilled off in vacuo at ca. 1 mbar and 110° C. In each case, a viscous, clear to slightly cloudy, virtually colorless product was obtained.

Table 2 lists the siloxanes produced by these general instructions GWI II.

TABLE 2

Prepared mixed alkyl- and polyether-modified or mixed alkyl- and glycerol-modified silicone products according to formula I ($R^1 = R^3$ = methyl)

| Product No. | Modification $R^2$ —CH₂CH₂CH₂O (EO)ₓ(PO)ᵧH | | Alkyl | p/o | a | b | c | d | e | f |
|---|---|---|---|---|---|---|---|---|---|---|
| | x | y | | | | | | | | |
| 13 | 8 | 0 | $C_{16}H_{33}$ | 1/3 | 0 | 12 | 228 | 0 | 10 | 0 |
| 14 | 8 | 0 | $C_{16}H_{33}$ | 1/3 | 0 | 16 | 227 | 0 | 0 | 7 |
| 15 | 8 | 0 | $C_{16}H_{33}$ | 1/5 | 8 | 0 | 73 | 25 | 0 | 3 |
| 16 | —CH₂CH₂CH₂OCH₂CH(OH)CH₂OH | | $C_{12}H_{25}$ | 9/15 | 0 | 12 | 228 | 0 | 10 | 0 |
| 17 | —CH₂CH₂CH₂OCH₂CH(OH)CH₂OH | | $C_{12}H_{25}$ | 9/16 | 8 | 0 | 73 | 25 | 0 | 3 |

Application Examples

All of the concentrations in the application examples are given in percent by weight. To prepare the emulsions, customary homogenization processes known to the person skilled in the art were used.

The formulation constituents are named in the compositions in the form of the generally recognized INCI nomenclature.

Emulsion Examples

These examples are intended to show that the emulsifiers according to the invention can be used in a large number of cosmetic formulations. Depending on the hydrophilicity of the emulsifiers according to the invention, it is possible to produce O/W or W/O emulsions. Moreover, with the help of the emulsifiers according to the invention, it is possible to stably incorporate pigments or solids into emulsion preparations. Furthermore, the examples show the good compatibility with typical coemulsifiers, oils, thickeners and stabilizers.

O/W Emulsion Examples

TABLE 3

Day cream to combat skin aging (antiaging):

| Example | 1 |
|---|---|
| Emulsifier 1 | 1.50% |
| Ceteareth-25 | 1.00% |
| Stearyl Alcohol | 1.50% |
| Glyceryl Stearate | 3.00% |
| Stearic Acid | 1.50% |
| Myristyl Myristate | 1.00% |
| Ceramide IIIB | 0.10% |
| Caprylic/Capric Triglyceride | 5.00% |
| Ethylhexyl Palmitate | 4.40% |
| Ethylhexyl Methoxycinnamate | 2.00% |
| Butyl Methoxydibenzoyl-methane | 1.00% |
| Glycerin | 3.00% |
| Water | ad 100% |
| TEGO ® Carbomer 134 (Carbomer) | 0.10% |
| Ethylhexyl Palmitate | 0.40% |
| Sodium Hydroxide (10% in water) | q.s. * |
| Preservative | q.s. |
| Perfume | q.s. |

* q.s. = quantum satis (Latin: as much as is necessary = sufficient amount)

TABLE 4

Self-tanning body lotion:

| Example | 2 |
|---|---|
| Emulsifier 5 | 1.00% |
| ABIL ® Care XL 80 (Bis-PEG/PPG-20/5 PEG/PPG-20/5 Dimethicone; Methoxy PEG/PPG-25/4 Dimethicone; Caprylic/Capric Triglyceride) | 1.00% |
| Cetearyl Isononanoate | 5.00% |
| Decyl Cocoate | 5.00% |
| Isopropyl Myristate | 5.00% |
| Sepigel ® 305 (Polyacrylamide; C13-14 Isoparaffin; Laureth-7) | 1.50% |
| PEG-30 Glyceryl Stearate | 2.00% |
| Dihydroxyacetone | 5.00% |
| Propylene Glycol | 3.00% |
| Water | ad 100% |
| Citric Acid | q.s. |
| Preservative | q.s. |
| Perfume | q.s. |

TABLE 5

Cationic sunscreen cream (in vitro SPF 18):

| Example | 3 |
|---|---|
| Emulsifier 1 | 2.00% |
| Distearyldimonium Chloride | 1.50% |
| Glyceryl Stearate | 2.00% |
| Stearyl Alcohol | 1.00% |
| C12-15 Alkyl Benzoate | 5.00% |
| TEGO ® Sun TDEC 45 (Tita-nium Dioxide; Diethyl-hexyl Carbonate; Poly-glyceryl-6 Polyhydroxy-stearate)) | 5.00% |
| Diethylhexyl Carbonate | 3.50% |

TABLE 5-continued

Cationic sunscreen cream (in vitro SPF 18):

| Example 3 | 3 |
|---|---|
| Cetyl Ricinoleate | 1.00% |
| Triisostearin | 1.00% |
| Octocrylene | 3.00% |
| Ethylhexyl Methoxycinnamate | 4.00% |
| Butyl Methoxydibenzoylmethane | 2.00% |
| Water | ad 100% |
| Glycerin | 3.00% |
| Preservative | q.s. |
| Perfume | q.s. |

TABLE 6

Skin-smoothing body lotion

| Example | 4 |
|---|---|
| Emulsifier 5 | 2.50% |
| Diethylhexyl Carbonate | 7.00% |
| Isopropyl Palmitate | 7.60% |
| Polysorbate 20 | 0.20% |
| Creatine | 0.50% |
| Panthenol | 0.50% |
| Glycerin | 3.00% |
| Water | ad 100% |
| TEGO ® Carbomer 341 ER (Acrylates/C10-30 Alkyl Acrylate Cross-polymer) | 0.30% |
| Xanthan Gum | 0.10% |
| Sodium Hydroxide (10% in water) | q.s. |
| TEGO ® Smooth Complex (Betaine; Urea; Potassium Lactate; Polyglutamic Acid; Hydrolyzed Sclerotium Gum) | 2.00% |
| Preservative | q.s. |
| Perfume | q.s. |

TABLE 7

Silky cream gel:

| Example | 5 |
|---|---|
| Emulsifier 5 | 4.00% |
| Cyclomethicone | 10.00% |
| Dimethicone | 3.00% |
| Cetyl Ricinoleate | 2.00% |
| Xanthan Gum | 0.20% |
| TECO ® Carbomer 341 ER (Acrylates/C10-30 Alkyl Acrylate Cross-polymer) | 0.40% |
| Caprylic/Capric Triglyceride | 1.90% |
| Water | ad 100% |
| Alcohol | 5.00% |
| Sodium Hydroxide (10% in water) | q.s. |
| Preservative | q.s. |
| Perfume | q.s. |

TABLE 8

O/W Impregnation emulsion for cosmetic wet wipes:

| | Example | 6 |
|---|---|---|
| A | TEGO ® Wipe DE (Diethylhexyl Carbonate; Polyglyceryl-4 Laurate; Phenoxyethanol; Methylparaben; Dilauryl Citrate; Ethylparaben; Butylparaben; Propylparaben; Isobutylparaben) | 5.70% |
| B | Water, demineralized | 5.70% |
| C | Emulsifier 1 | 0.30% |
| | Creatine | 0.25% |

TABLE 8-continued

O/W Impregnation emulsion for cosmetic wet wipes:

| | Example | 6 |
|---|---|---|
| | Panthenol | 0.50% |
| | Water, demineralized | 87.55 |
| Z | Perfume | q.s. |

Preparation: At room temperature, A is firstly mixed with B, then C and Z are added with stirring.

W/O Emulsion Examples

TABLE 9

Water-in-silicone oil lotion:

| Example | 7 | 8 | 9 |
|---|---|---|---|
| Emulsifier 3 | 2.00% | | |
| Emulsifier 13 | | 2.00% | |
| Emulsifier 17 | | | 2.00% |
| Cyclopentasiloxane | 19.50% | 19.50% | 19.50% |
| Sodium Chloride | 0.50% | 0.50% | 0.50% |
| Glycerin | 3.00% | 3.00% | 3.00% |
| Water | ad 100% | ad 100% | ad 100% |
| Preservative | q.s. | q.s. | q.s. |
| Perfume | q.s. | q.s. | q.s. |

TABLE 10

Water-resistant sunscreen:

| Example | 10 | 11 | 12 |
|---|---|---|---|
| Emulsifier 6 | 2.50% | | |
| Emulsifier 15 | | 2.50% | |
| Emulsifier 16 | | | 2.50% |
| C12-15 Alkyl Benzoate | 10.00% | 10.00% | 10.00% |
| Paraffinum Perliquidum | 13.50% | 13.50% | 13.50% |
| Cetyl Dimethicone | 1.00% | 1.00% | 1.00% |
| Titanium Dioxide | 5.00% | 5.00% | 5.00% |
| Sodium Chloride | 0.50% | 0.50% | 0.50% |
| Water | ad 100% | ad 100% | ad 100% |
| Preservative | q.s. | q.s. | q.s. |
| Perfume | q.s. | q.s. | q.s. |

TABLE 11

Make-up foundation:

| Example | 13 | 14 | 15 |
|---|---|---|---|
| Emulsifier 8 | 3.50% | | |
| Emulsifier 15 | | 3.50% | |
| Emulsifier 17 | | | 3.50% |
| Diethylhexyl Carbonate | 10.00% | 10.00% | 10.00% |
| Cyclopentasiloxane | 12.60% | 12.60% | 12.60% |
| Iron Oxides | 1.80% | 1.80% | 1.80% |
| Titanium Dioxide | 7.20% | 7.20% | 7.20% |
| Talc | 2.00% | 2.00% | 2.00% |
| Ethylhexyl Palmitate | 3.40% | 3.40% | 3.40% |
| Sodium Chloride | 1.00% | 1.00% | 1.00% |
| Glycerin | 2.00% | 2.00% | 2.00% |
| Water | ad 100% | ad 100% | ad 100% |
| Preservative | q.s. | q.s. | q.s. |
| Perfume | q.s. | q.s. | q.s. |

Examples of the Use as Hydrophobic Emollient

The two examples below are intended to show that products according to the invention can sometimes also be used as hydrophobic or lipophilic emollients in cosmetic formulations and lead here to good sensory properties.

TABLE 12

Sun lotion W/O (in vitro SPF 50+):

| | Example | 16 | 17 |
|---|---|---|---|
| A | Isolan ® GPS (Polyglyceryl-4 Diisostearate/Polyhydroxystearate/Sebacate) | 3.00% | 3.00% |
| | Product 10 | 0.40% | |
| | Product 11 | | 0.40% |
| | Zinc Stearate | 1.00% | 1.00% |
| | Tego ® Sun TDEC 45 (Titanium Dioxide; Diethylhexyl Carbonate; Polyglyceryl-6 Polyhydroxystearate) | 22.00% | 22.00% |
| | Ethylhexyl Methoxycinnamate, Diethylamino Hydroxybenzoyl Hexyl Benzoate | 10.00% | 10.00% |
| | Ethylhexyl Salicylate | 5.00% | 5.00% |
| | Bis-Ethylhexyloxyphenol Methoxyphenyl Triazine (BEMT, Ciba) | 3.00% | 3.00% |
| | Preservative | q.s. | q.s. |
| B | Glycerin | 3.00% | 3.00% |
| | Magnesium Sulfate Heptahydrate | 1.50% | 1.50% |
| | Water | 51.10% | 51.10% |
| Z | Perfume | q.s. | q.s. |

Preparation: A is heated to 80° C. and, with stirring, B is added and homogenized. The mixture is then left to cool to 30° C. with gentle stirring, Z is added and the mixture is homogenized again.

TABLE 13

O/W hand cream (hand care treatment):

| | | Example 18 |
|---|---|---|
| A | Glyceryl Stearate SE | 6.00% |
| | Cetearyl Alcohol | 2.00% |
| | Stearic Acid | 2.00 |
| | Ethylhexyl Stearate | 3.00% |
| | Mineral Oil (30 mPas) | 3.00% |
| | Dimethicone (350 mPas) | 1.50% |
| | Product 11 | 2.00% |
| B | Glycerin | 7.00% |
| | Panthenol | 0.50% |
| | Water | 73.00% |
| | Preservative, Perfume | q.s. |

Preparation: A and B are heated separately to 70-75° C. Then, with stirring, A is added to B and homogenized. The mixture is cooled with gentle stirring.

Examples of Rinse-Off Applications

Testing the conditioning of skin (skincare performance) and foam properties by means of a handwashing test:

To evaluate the conditioning of skin (skincare performance) and the foam properties of the organomodified siloxane according to the invention branched in the silicone part product No. 5 in aqueous, surface-active formulations, sensory handwashing tests compared to the comparative example product No. 12 according to the prior art were carried out.

The comparison product 12 is widespread in industry as care active ingredients and regarded as highly effective care active ingredient in aqueous, surface-active formulations.

A group consisting of ten trained test subjects washed their hands in a defined manner and evaluated foam properties and skin feel using a grading scale from 1 (poor) to 5 (very good).

The products used were in each case tested in a standardized surfactant formulation (Table 14).

A formulation without addition of a polyethersiloxane is used as control formulation 19.

TABLE 14

Test formulations for handwashing test:

| | Formulation examples | | |
|---|---|---|---|
| | 19 | 20 | C21 |
| Texapon NSO ®, 28% strength, Cognis (INCI: Sodium Laureth Sulfate) | 32% | 32% | 32% |
| TEGO Betain F 50 ®, 38% strength, Evonik Goldschmidt GmbH (INCI: Cocamidopropyl Betaine) | 8% | 8% | 8% |
| Sodium Chloride | 2% | 2% | 2% |
| Water, demineralized | ad 100.0% | | |
| Product No. 5 (according to the invention) | | 0.5% | |
| Product No. 12 (not according to the invention) | | | 0.5% |

The sensory test results are summarized in Table 15.

TABLE 15

Results of the handwashing test:

| | Test formulation | | |
|---|---|---|---|
| | 19 | 20 | C21 |
| Foaming behavior | 3.0 | 3.8 | 3.3 |
| Foam volume | 2.8 | 3.4 | 3.0 |
| Foam creaminess | 2.3 | 3.4 | 2.9 |
| Skin feel during washing | 2.8 | 3.9 | 3.6 |
| Skin smoothness | 1.4 | 3.0 | 2.7 |
| Skin softness | 2.0 | 2.9 | 2.6 |
| Skin smoothness after 3 min | 2.6 | 3.8 | 3.4 |
| Skin softness after 3 min | 2.5 | 3.9 | 3.6 |

The results of the handwashing test are shown in Table 15. It is clear from the measurement results that the formulation 20 according to the invention with use of the product No. 5 according to the invention is superior in all application properties compared to the comparison formulation C21 according to the prior art. Against this background, the results of the formulation 20 according to the invention are to be deemed very good.

It is clear by reference to the measurement values that the product No. 5 according to the invention in formulation 20 leads to an improvement in skin properties and foam properties compared to product No. 12 in formulation C21.

Furthermore, the measurement values reveal that the control formulation 19 without a polyethersiloxane compound has poorer measurement values than formulations 20 and C21.

Testing the Conditioning of Hair by Means of Sensory Tests:

For the application-related assessment of the conditioning of hair, the product No. 5 according to the invention and the comparison product No. 12 were used in simple cosmetic formulations (shampoo and hair rinse).

The Application Properties Upon Use in a Shampoo were Investigated in the Following Formulations:

TABLE 16

Shampoo formulations for testing the hair-conditioning properties:

| | Formulation examples | | |
|---|---|---|---|
| | 22 | 23 | C24 |
| Texapon NSO ®, 28% strength, Cognis (INCI: Sodium Laureth Sulfate) | 32% | 32% | 32% |
| TEGO Betain F 50 ®, 38% strength, Evonik Goldschmidt GmbH (INCI: Cocamidopropyl Betaine) | 8% | 8% | 8% |
| Jaguar 162, Rhodia (INCI: Guar Hydroxypropyl trimonium Chloride) (cationic polymer for improving the effectiveness of conditioners) | 0.3% | 0.3% | 0.3% |
| Water, demineralized | ad 100.0% | | |
| Citric acid | ad pH 6.0 ± 0.3 | | |
| Product No. 5 (according to the invention) | | 0.5% | |
| Product No. 12 (not according to the invention) | | | 0.5% |

To evaluate the properties of the shampoo formulation, no post-treatment with a rinse was carried out in the course of the test.

The Application Properties Upon Use in Hair Rinses were Examined in the Following Formulations:

TABLE 17

Hair rinse formulations for testing the hair-conditioning properties:

| | Formulation examples | | |
|---|---|---|---|
| | 25 | 26 | C27 |
| TEGINACID ® C, Evonik Goldschmidt GmbH (INCI: Ceteareth-25) | 0.5% | 0.5% | 0.5% |
| TEGO ® Alkanol 16, Evonik Goldschmidt GmbH (INCI: Cetyl Alcohol) | 4% | 4% | 4% |
| VARISOFT ® 300, 30% strength, Evonik Goldschmidt GmbH (INCI: Cetrimonium Chloride) | 3.3% | 3.3% | 3.3% |
| Water, demineralized | ad 100.0% | | |
| Citric acid | ad pH 4.0 ± 0.3 | | |
| Product No. 5 (according to the invention) | | 0.5% | |
| Product No. 12 (not according to the invention) | | | 0.5% |

In the case of the property testing of hair rinses, the hair is pretreated using a shampoo which does not contain conditioners.

For the application-related assessment, hair tresses which are used for sensory tests are predamaged in a standardized manner by a permanent wave treatment and a bleaching treatment. For this, customary styling products are used. The test procedure, the base materials used and also the details of the assessment criteria are described in DE 10327871.

Standardized treatment of predamaged hair tresses with conditioning samples:

The predamaged hair tresses, as described above, are treated as follows with the shampoo described above or the conditioning rinse described above:

The hair tresses are wetted under running warm water. The excess water is gently squeezed out by hand, then the shampoo is applied and gently worked into the hair (1 ml/hair tress (2 g)). After a residence time of 1 min, the hair is rinsed for 1 min.

If necessary, directly afterward, the rinse is applied and gently worked into the hair (1 ml/hair tress (2 g)). After a residence time of 1 min, the hair is rinsed for 1 min.

Prior to the sensory assessment, the hair is dried in the air at 50% atmospheric humidity and 25° C. for at least 12 h.

Assessment Criteria:

The sensory assessments are made using grades which are awarded on a scale from 1 to 5, with 1 being the poorest evaluation and 5 being the best evaluation. The individual test criteria are each given their own evaluation.

The test criteria are: wet combability, wet feel, dry combability, dry feel, appearance/shine.

Table 18 below compares the results of the sensory assessment of the hair tresses carried out as described above with the formulation 23 according to the invention, the comparison formulation C24 and the control formulation 22 (placebo without test substance).

TABLE 18

Results of the conditioning of hair from shampoo formulation:

|  | Wet combability | Wet feel | Dry combability | Dry feel | Shine |
|---|---|---|---|---|---|
| Formulation 23 according to the invention | 3.8 | 3.8 | 4.3 | 4.3 | 3.9 |
| Comparison formulation C24 (not according to the invention) | 3.0 | 3.0 | 3.0 | 3.5 | 3.0 |
| Control formulation 22 (placebo) | 2.3 | 2.5 | 2.8 | 3.3 | 2.3 |

Surprisingly, the results show that the formulation 23 according to the invention with product No. 5 according to the invention are given significantly better evaluations than the comparison formulation C24 with the product No. 12 according to the prior art. The good evaluation of the shine properties of all of the formulations according to the invention is particularly clearly emphasized.

TABLE 19

Results of the conditioning of hair from hair rinse formulations:

|  | Wet combability | Wet feel | Dry combability | Dry feel | Shine |
|---|---|---|---|---|---|
| Formulation 26 according to the invention | 4.7 | 5.0 | 4.8 | 4.7 | 4.6 |
| Comparison formulation C27 (not according to the invention) | 4.5 | 4.2 | 4.5 | 4.3 | 3.8 |
| Control formulation 25 | 3.8 | 3.9 | 4.0 | 3.8 | 2.9 |

In the hair rinse application as well, the formulation according to the invention with product No. 5 according to the invention exhibits very good cosmetic evaluations in the sensory assessment. In this connection, the already very good properties of the comparison formulation C27 with the comparison product No. 12 were yet further increased by the formulation 26 according to the invention with the compound No. 5 according to the invention.

A significantly better evaluation is also achieved in the case of the shine through the use of the formulation 26 according to the invention.

Further Formulation Examples

These examples are intended to show that the siloxanes according to the invention can be used in a large number of cosmetic formulations.

TABLE 20

Hair shampoo with conditioner (conditioning shampoo):

| | |
|---|---|
| TEXAPON ® NSO, Cognis, 28% strength (INCI: Sodium Laureth Sulfate) | 25% |
| Perfume | 0.3% |
| Product No. 5 (according to the invention) | 0.5% |
| ABIL ® Quat 3272, Evonik Goldschmidt GmbH (INCI: Quaternium-80) | 0.5% |
| PLANTACARE ® 1200 UP, Cognis 50% (INCI: Lauryl Glycoside) | 4.25% |
| Water | 54.7% |
| TEGO ® Betain F 50, Evonik Goldschmidt GmbH, 38% strength (INCI: Cocamidopropyl Betaine) | 14.25% |
| ANTIL ® 171, Evonik Goldschmidt GmbH (INCI: PEG-18 Glyceryl Oleate/Cocoate) | 0.5% |

TABLE 21

Moisturizing body wash lotion:

| | |
|---|---|
| TEXAPON ® NSO, Cognis, 28% strength (INCI: Sodium Laureth Sulfate) | 30% |
| TEGOSOFT ® PC 31, Evonik Goldschmidt GmbH, (INCI: Polyglyceryl-3 Caprate) | 0.5% |
| Product No. 5 (according to the invention) | 0.3% |
| Perfume | 0.3% |
| Water | 54.1% |
| TEGOCEL ® HPM 4000, Evonik Goldschmidt GmbH (INCI: Hydroxypropyl Methylcellulose) | 0.3% |
| REWOTERIC ® AM C, Evonik Goldschmidt GmbH, 32% strength (INCI: Sodium Cocoamphoacetate) | 10% |
| Citric Acid Monohydrate | 0.5% |
| REWODERM ® LI S 80, Evonik Goldschmidt GmbH (INCI: PEG-200 Hydrogenated glyceryl Palmate; PEG-7 Glyceryl Cocoate) | 2% |
| TEGO ® Pearl N 300, Evonik Goldschmidt (INCI: Glycol Distearate; Laureth-4; Cocamidopropyl Betaine) | 2% |

TABLE 22

Body cleansing foam:

| | |
|---|---|
| TEXAPON ® NSO, Cognis, 28% strength (INCI: Sodium Laureth Sulfate) | 14% |
| Perfume | 0.3% |
| Product No. 5 (according to the invention) | 0.5% |
| REWOTERIC ® AM C, Evonik Goldschmidt GmbH, 32% strength (INCI: Sodium Cocoamphoacetate) | 8% |
| Water | 75.2% |
| TEGOCEL ® HPM 50, Evonik Goldschmidt GmbH (INCI: Hydroxypropyl Methylcellulose) | 0.5% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1% |
| Citric Acid Monohydrate | 0.5% |

TABLE 23

Mild shower bath:

| | |
|---|---|
| TEXAPON ® NSO, Cognis, 28% strength (INCI: Sodium Laureth Sulfate) | 27% |
| REWOPOL ® SB FA 30, Evonik Goldschmidt GmbH, 40% strength (INCI: Disodium Laureth Sulfosuccinate) | 12% |
| TEGOSOFT ® LSE 65 K SOFT, Evonik Goldschmidt GmbH, (INCI: Sucrose Cocoate) | 2% |
| Water | 39% |
| REWOTERIC ® AM C, Evonik Goldschmidt GmbH, 32% strength (INCI: Sodium Cocoamphoacetate) | 13% |
| Product No. 5 (according to the invention) | 0.5% |
| Citric acid (30% in water) | 3% |
| ANTIL ® 171 Evonik Goldschmidt GmbH (INCI: PEG-18 Glyceryl Oleate/Cocoate) | 1.5% |

TABLE 23-continued

Mild shower bath:

| | |
|---|---|
| TEGO ® Pearl N 300, Evonik Goldschmidt (INCI: Glycol Distearate; Laureth-4; Cocamidopropyl Betaine) | 2% |

TABLE 24

Hair conditioner:

| | | |
|---|---|---|
| A | Water | 93.75% |
| | Propylene Glycol | 1% |
| | Citric acid Monohydrate | q.s. |
| B | TEGO ® ALKANOL 16, Evonik Goldschmidt GmbH (INCI: Cetyl alcohol | 3% |
| | VARISOFT ® PATC, Evonik Goldschmidt GmbH (INCI: Palmitamidopropyltrimonium Chloride) | 1.75% |
| | Product No. 5 (according to the invention) | 0.5% |
| C | Perfume, preservative | q.s. |

TABLE 25

Hair repair leave-in conditioner spray:

| | |
|---|---|
| TAGAT ® CH-40, Evonik Goldschmidt GmbH (INCI: PEG-40 Hydrogenated Castor Oil) | 2% |
| Ceramide VI, Evonik Goldschmidt GmbH (INCI: Ceramide 6 II) | 0.05% |
| Perfume | 0.2% |
| Water | 89.75% |
| Product No. 5 (according to the invention) | 2.0% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 2% |
| TEGO ® Betain F 50 Evonik Goldschmidt GmbH 38% (INCI: Cocamidopropyl Betaine) | 2% |
| Citric Acid (10% in water) | 2% |

TABLE 26

Leave-in conditioning mousse:

| | |
|---|---|
| Product No. 5 (according to the invention) | 0.5% |
| ABIL ® B 88183, Evonik Goldschmidt GmbH (INCI: PEG/PPG-20/6 Dimethicone) | 0.4% |
| TAGAT ® CH-40 (INCI: PEG-40 Hydrogenated Castor Oil) | 0.5% |
| Perfume | 0.2% |
| TEGO ® Betain 810, Evonik Goldschmidt GmbH, 38% strength (INCI: Capryl/Capramidopropyl Betaine) | 4% |
| Water | 93.5% |
| Panthenol | 0.2% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 0.3% |
| Citric Acid (30% in water) | 0.4% |

TABLE 27

Creamy shaving foam:

| | | |
|---|---|---|
| A | Water | 50% |
| | Coconut Fatty Acid | 1.4% |
| | Monoethanolamine | 1.3% |
| | Myristic Acid | 3.5% |
| B | TEGOSOFT ® LSE 65 K Evonik Goldschmidt (INCI: Sucrose Cocoate) | 2% |
| C | TEGO ® Betain 810 Evonik Goldschmidt (INCI: Capryl/Capramidopropyl Betaine) | 7.6% |
| | Glycerin | 5% |
| | Product No. 5 (according to the invention) | 1.7% |
| | Perfume | 0.3% |
| | Water | 26.5% |

TABLE 27-continued

Creamy shaving foam:

| | |
|---|---|
| TEGOCEL ® HPM 50 Evonik Goldschmidt (INCI: Hydroxypropyl Methylcellulose) | 0.7% |

The invention claimed is:

1. A formulation comprising an organomodified siloxane branched in the siloxane part, wherein the organomodified siloxane is a compound of formula I $$M_a M'_b D_c D'_d T_e Q_f \quad \text{formula I}$$

wherein
$M=(R^1{}_3SiO_{1/2})$
$M'=(R^2R^1{}_2SiO_{1/2})$
$D=(R^1{}_2SiO_{2/2})$
$D'=(R^2R^1SiO_{2/2})$
$T=(R^3SiO_{3/2})$
$Q=(SiO_{4/2})$
a=0 to 14;
b=1 to 14;
with the proviso that
a+b>2;
c=20 to 400;
d=0;
e=2 to 15;
f=0 to 15;
with the proviso that
e+f≥3;
$R^1$=methyl,
$R^2$=a polyether radical of general formula IIa:

$$CH_2-CH_2-(CH_2)_n O(EO)_x(PO)_y(XO)_z R^4 \quad \text{formula IIa}$$

where
$EO=(C_2H_4O)$;
$PO=(C_3H_6O)$
$XO=(C_2H_3R^5O)$;
n=1;
x=5 to 30;
y=2 to 20;
z=0;
$R^4$=H;
$R^3$=independently of one another, identical or different radicals $R^1$ or $R^2$.

2. The formulation of claim 1, wherein said organomodified siloxane is prepared by hydrosilylation or unsaturated polyether with SiH-functional siloxane block copolymers branched in the silicone part and liquid at a temperature of 25° C., where the SiH-functional siloxane block copolymers are prepared by reacting a mixture comprising
   a) one or more SiH-functional siloxanes,
   b) one or more SiH-function-free siloxanes, and
   c) one or more tetraalkoxysilanes,
      and optionally
   d) one or more trialkoxysilanes
   with the addition of water and in the presence of at least one solid Brönsted-acidic catalyst, which is selected from the acidic ion exchangers, in one process step.

3. The formulation of claim 1, wherein said organomodified siloxane is a component of one of an oil-in-water (O/W) emulsion and a water-in-oil (W/O) emulsion.

4. The formulation of claim 1, further inorganic or organic pigments and at least one of inorganic particles and organic particles.

5. The formulation of claim 1, wherein said organomodified siloxane is an additive for a cosmetic or pharmaceutical formulation for improving sensory properties and/or for the conditioning of skin and/or hair.

6. The formulation of claim 1, wherein said organomodified siloxane is a care active ingredient for the home or industry.

7. The formulation of claim 1, wherein said organomodified siloxane is an emulsifier in care creams and lotions for face, body and hands, in sunscreen emulsions, in make-up, in aerosols, roll-ons, pump sprays, sticks, in the antiperspirant/deodorant sector, in babycare products, in intimate care, footcare, haircare, nail care, dental care or oral care products, and also in dermatological ointments.

8. The formulation of claim 1, wherein said formulation is an aqueous care formulation or a surface-active, cosmetic, dermatological or pharmaceutical formulation for shower baths and/or shower gels, bath formulations, liquid soaps and shampoos, skin masks, shaving foams, hair rinses, leave-in conditioners and/or styling products for hair.

9. A preparation comprising an organomodified siloxane branched in the silicone part, wherein said organomodified siloxane is a compound of formula I $$M_a M'_b D_c D'_d T_e Q_f \qquad \text{formula I}$$

wherein
$M=(R^1{}_3 SiO_{1/2})$
$M'=(R^2 R^1{}_2 SiO_{1/2})$
$D=(R^1{}_2 SiO_{2/2})$
$D'=(R^2 R^1 SiO_{2/2})$
$T=(R^3 SiO_{3/2})$
$Q=(SiO_{4/2})$
a=0 to 14;
b=1 to 14;
with the proviso that
a+b>2;
c=20 to 400;
d=0;
e=2 to 15;
f=0 to 15;
with the proviso that
e+f≥3;
$R^1$ methyl,
$R^2$=a polyether radical of general formula IIa:

$$CH_2-CH_2-(CH_2)_n O(EO)_x (PO)_y (XO)_z R^4 \qquad \text{formula IIa}$$

where
$EO=(C_2H_4O)$;
$PO=(C_3H_6O)$;
$XO=(C_2H_3R^5O)$;
n=1;
x=5 to 30;
y=2 to 20;
z=0;
$R^4$=H;

$R^3$=independently of one another, identical or different radicals $R^1$ or $R^2$.

10. A cosmetic, dermatological or pharmaceutical formulation comprising at least a preparation in the form of an emulsion, said preparation comprising an organomodified siloxane in the silicone part, wherein said organomodified siloxane is a compound of formula I $$M_a M'_b D_c D'_d T_e Q_f \qquad \text{formula I}$$

wherein
$M=(R^1{}_3 SiO_{1/2})$
$M'=(R^2 R^1{}_2 SiO_{1/2})$
$D=(R^1{}_2 SiO_{2/2})$
$D'=(R^2 R^1 SiO_{2/2})$
$T=(R^3 SiO_{3/2})$
$Q=(SiO_{4/2})$
a=0 to 14;
b=1 to 14;
with the proviso that
a+b>2
c=20 to 400;
d=0;
e=2 to 15;
f=0 to 15;
with the proviso that
e+f≥3;
$R^1$ methyl,
$R^2$=a polyether radical of general formula IIa:

$$CH_2-CH_2-(CH_2)_n O(EO)_x (PO)_y (XO)_z R^4 \qquad \text{formula IIa}$$

where
$EO=(C_2H_4O)$;
$PO=(C_3H_6O)$;
$XO=(C_2H_3R^5O)$;
n=1;
x=5 to 30;
y=2 to 20;
z=0;
$R^4$=H.

11. A care and cleaning composition for the home, for hard surfaces, leather or textiles comprising a preparation in the form of an emulsion, wherein said preparation comprises a formulation according to claim 1.

12. The care and/or cleaning of claim 11 further comprising particles or pigments as an additional component.

13. The formulation of claim 1, further comprising at least one cosmetic active ingredient as an additional component.

14. The formulation of claim 1, further comprising at least one pharmaceutical active ingredient as an additional component.

15. The formulation of claim 1, further comprising at least one dermatological active ingredient as an additional component.

* * * * *